United States Patent [19]

Wildemeersch

[11] Patent Number: 4,684,369

[45] Date of Patent: Aug. 4, 1987

[54] INSTRUMENT FOR SUPRAPUBIC DRAINAGE OF THE BLADDER, INSERTED THROUGH THE URETHRA

[76] Inventor: Dirk A. A. Wildemeersch, Pierslaan, 125, B-8300 Knokke-Heist, Belgium

[21] Appl. No.: 767,238

[22] Filed: Aug. 19, 1985

Related U.S. Application Data

[63] Continuation of Ser. No. 484,564, Apr. 13, 1983, abandoned.

[30] Foreign Application Priority Data

Apr. 14, 1982 [BE] Belgium .............................. 0/207.811
Jun. 28, 1982 [BE] Belgium .............................. 0/208.473

[51] Int. Cl.⁴ .............................................. A61M 5/32
[52] U.S. Cl. .................................... 604/272; 604/264; 128/329 R
[58] Field of Search ............ 604/160, 161, 166, 51–53, 604/55, 158–159, 162–165, 167–170, 264, 272, 280, 283; 128/305.3, 314, 328, 329 R

[56] References Cited

U.S. PATENT DOCUMENTS

| | | | |
|---|---|---|---|
| 3,384,087 | 5/1968 | Brummelkamp ................. | 128/305.3 |
| 3,608,539 | 9/1971 | Miller .................... | 128/314 |
| 3,640,281 | 2/1972 | Robertson ................ | 604/264 |
| 3,651,807 | 3/1972 | Huggins . | |
| 3,742,958 | 7/1973 | Rundles .................. | 604/160 |
| 3,777,743 | 12/1973 | Binard et al. ................. | 128/305 |
| 3,780,733 | 12/1973 | Martinez-Manzor .............. | 604/158 |
| 3,788,326 | 1/1974 | Jacobs .................. | 604/161 |
| 3,826,256 | 7/1974 | Smith .................... | 604/159 |
| 3,861,391 | 1/1975 | Antonevich et al. ............. | 128/328 |
| 3,920,023 | 11/1975 | Dye et al. . | |
| 4,239,042 | 12/1980 | Asai . | |
| 4,275,724 | 6/1981 | Behrstock ..................... | 604/164 |
| 4,345,596 | 8/1982 | Young .................... | 604/161 |
| 4,385,631 | 5/1983 | Uthmann ................... | 604/53 |
| 4,405,314 | 9/1983 | Cope ..................... | 604/51 |
| 4,573,576 | 3/1986 | Krol ..................... | 604/280 |

FOREIGN PATENT DOCUMENTS

| | | | |
|---|---|---|---|
| 181354 | 3/1955 | Fed. Rep. of Germany ...... | 604/158 |
| 791563 | of 0000 | France .................. | 604/160 |
| 2161950 | 7/1973 | France . | |
| 174760 | 9/1965 | U.S.S.R. ................ | 604/272 |

OTHER PUBLICATIONS

Suprapubic Cystostomy by Trocar Catheter: A Preliminary Report, J. M. Ingram, M.D.
Suprapubic Cystostomy and the Use of Polyethylene Tubing, by B. D. Taylor, M.D. et al.
Trocar Suprapubic Cystostomy for Postoperative Bladder Drainage in the Female, by C. Paul Hodgkins, M.D. et al.
Instrument and Method, Bladder Drainage with the Suprapubic Catheter Needle, by P. J. Bonanno, M.D. et al.
Use of Suction with Suprapubic Bladder Drainage, by D. H. Kariher, M.D. et al.
Needle Suprapubic Cystostomy, A New and Simple Technique, by A. H. Ansari, M.D. et al.

Primary Examiner—C. Fred Rosenbaum
Assistant Examiner—Gene B. Kartchner
Attorney, Agent, or Firm—Weingarten, Schurgin, Gagnebin & Hayes

[57] ABSTRACT

A suprapublic instrument for drainage of the bladder inserted through the urethra, characterized in that it includes at least one curved needle having a sharp tip at its end and fitted with means for connecting it to a catheter, a catheter designed to act as a drain, and a sound or sleeve designed to be introduced into the ureter, so constructed that the needle and the catheter are able to pass through it.

12 Claims, 12 Drawing Figures

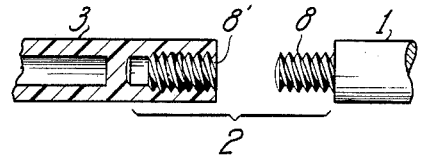
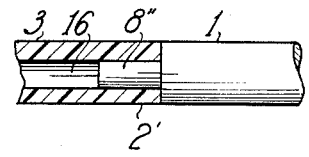
FIG.5  FIG.6
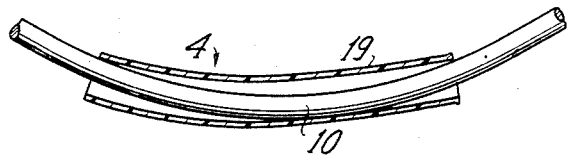
FIG.7
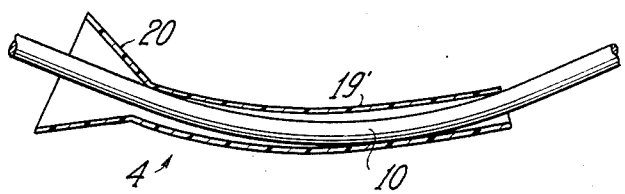
FIG.8
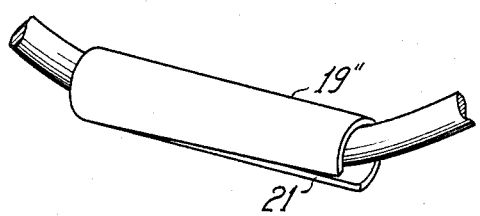
FIG.9
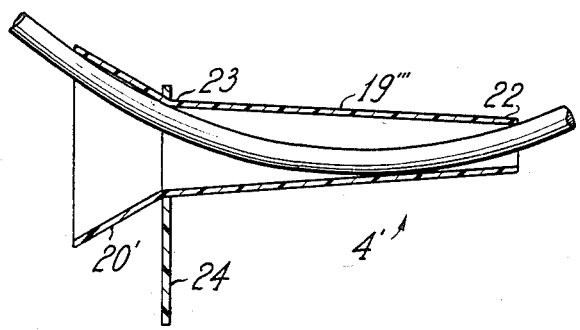
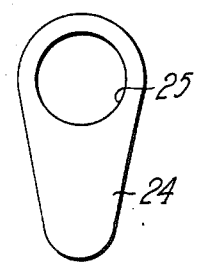
FIG.10  FIG.11

INSTRUMENT FOR SUPRAPUBIC DRAINAGE OF THE BLADDER, INSERTED THROUGH THE URETHRA

This application is a continuation of application Ser. No. 484,564, filed Apr. 13, 1983, now abandoned.

FIELD AND BACKGROUND OF THE INVENTION

Instruments for suprapubic drainage of the bladder have been known for a long time, especially in surgery on men.

Over the past few years a technique has been developed for suprapubic drainage of the bladder in surgery on women which makes use of smaller-diameter catheters.

The advantages of a suprapubic bladder drainage instrument over the instrument for drainage through the urethra which has long been used on surgery on women (Foley catheter) have been established by numerous research projects and reports published from the 1960's to the present day.

The recognized advantages of such instruments are, most importantly:
  increased comfort for the patient;
  significant reduction in causes of infection;
  significant reduction of hospital care during the period of bladder drainage;
  patient's ability to begin normal urination while the catheter is still in place.

However, all the suprapubic bladder drainage instruments known to date are designed to be introduced into the bladder through the abdominal wall. This type of procedure requires the intervention of a specialist so that the catheter can be introduced into the bladder safely, without any damage to neighboring organs.

SUMMARY OF THE INVENTION

In accordance with the teaching of the present invention there is provided an instrument for suprapubic drainage of the bladder which can be introduced through the urethra. This procedure makes the placement of the catheter much simpler, since it is done from the bladder in the direction of the abdominal wall, passing around the symphysis. Thus the catheter can be counted on to advance into the bladder without any risk of perforating it on either side, it is also much easier to position the point of puncture of the abdominal wall correctly from the bladder. Thus a specialist is no longer required for introducing a catheter with this type of instrument.

One object of the invention, therefore, is to provide an instrument for suprapubic drainage of the bladder inserted through the urethra, which includes at least:
  one curved needle, with a sharp tip at its front end, equipped with means for connecting it to a catheter;
  a catheter designed to serve as the drain;
  a sound or sleeve, designed to be introduced into the urethra, constructed so that it allows the needle and the catheter to pass through it.

Another object of the invention is to furnish a needle for the introduction through the urethra of a suprapubic bladder drainage instrument, this needle consisting of two portions: a front portion constituting the active part of the needle, terminating at the front end in a sharp tip and joined at the rear to a back portion constituting the gripping and manipulating element of the needle, at least the front portion being at least partly curved, the curvature being such that the tip forms an angle of between 115° and 145° with the rear of the active part, the needle being equipped with means for connecting it to a catheter.

In another characteristic of the invention, the front portion of the needle consists of a stright head portion from which the tip is formed, extended by a part in the form of an arc of a circle with an angle at the center of 35° to 65° and a radius of curvature of 6 to 10 cm, this part in the form of an arc of a circle being connected to a straight part constituting the rear of the active part, which extends to form the gripping and manipulating element.

In still another characteristic of the invention, in the back portion making up the gripping and manipulating element of the needle there is at least one seat designed to accommodate a pin formed on the bottom surface of a thumb piece, to furnish a temporary connection between said thumb piece and the needle.

In still another characteristic of the invention, extending into the back portion of the needle are at least two diametrically aligned holes designed to accommodate two pins formed on the bottom surface of the thumb piece, these pins being formed in the median part of a semicylindrical groove conforming to the shape of the body of the needle.

In still another characteristic of the invention, the front portion and the back portion of the needle are curved.

In another characteristic of the invention, the means for connecting the needle to a catheter consist of an interlocking device located at the end of the back portion of the needle.

In still another characteristic of the invention, the interlocking device at the end of the back area of the needle is one of the elements of a screw-threaded interlocking device, and the outer dimensions of this interlocking device in crosssection do not exceed the outer dimensions of the needle in cross-section.

In another characteristic of the invention, the interlocking device at the end of the back portion of the needle is a stud coaxial with the needle, whose diameter matches the inner diameter of the catheter, designed to be inserted into the front end of said catheter and joined to it by an adhesive.

In another characteristic of the invention, the means for connecting the needle to a catheter consist of a lengthwise canal inside the needle through which the catheter is able to pass.

Another object of the invention is to furnish a catheter designed to serve as a suprapubic drain for the bladder, which, so that it can be connected to a needle terminating in an interlocking device, has at one end an interlocking device which fits together with that provided at the end of the needle, and at the other end a perforated part constituting the drainage instrument, the outer dimensions of the catheter in cross-section being no greater than the outer dimensions of the needle in cross-section.

In another characteristic of the invention, the catheter has reference marks on its outer surface which indicate the distance between that point and the drainage tip.

Still another object of the invention is to furnish a sound or sleeve for the introduction through the urethra of a suprapubic drainage instrument for the bladder, which possesses a tubular body constituting a canal whose internal dimensions in cross-section are at least slightly larger than the external dimensions in cross-section of the needle, means being provided to allow the passage of the curved needle.

In another characteristic of the invention, the body of the sound or sleeve is of adequate flexibility so that it can be deformed to allow the needle to pass through.

In still another characteristic of the invention, the body of the sound or sleeve is straight and its flexibility is enhanced by the presence of a lengthwise slit extending from the front of the sleeve body over a distance of between half and all of the length of the sleeve body.

In another characteristic of the invention, the body of the sleeve has a curvature which roughly matches that of the most curved part of the needle, and it is flexible enough so that the other parts of the needle can pass through it.

In another characteristic of the invention, the body of the sleeve is made of a stiff material and its shape is roughly that of a truncated cone whose diameter increases from its anterior to its posterior part, and the dimensions of the truncated-cone-shaped canal which it forms are sufficient to allow the curved needle to pass through.

In still another characteristic of the invention, the body of the sleeve is followed by an opening which widens from the body to its posterior end, said opening being equipped with means for connection to a syringe.

In another characteristic of the invention, the sleeve has a gripping element, roughly flat in shape, on the posterior part of the body, said element extending transversely to the body and serving as the retaining device for keeping the sleeve in active position.

In still another characteristic of the invention, the gripping element is detachable and is in the form of a plate machined with an opening whose size matches the cross-section of the sleeve body, this plate being slid onto the sleeve body until it is stopped by the flared opening of the sleeve.

DESCRIPTION OF THE DRAWING

These and other objects will be more fully understood by reference to the following solely examplary description and the attached drawing, which gives various embodiments of the invention solely by way of example, and in which;

FIG. 5 is a partially sectional view, on a larger scale, of an interlocking device to connect a needle and a catheter, according to the invention;

FIG. 6 is a partially sectional view of another embodiment of an interlocking device to connect a needle and a catheter, according to the invention;

FIG. 7 is a partially sectional view of the body of a sleeve or sound made of flexible material deforming during the passing of a curved part of a needle;

FIG. 8 is a partially sectional view of a curved sleeve during the passage of a curved part of a needle;

FIG. 9 is a perspective view of the body of a straight sleeve, provided with a lengthwise slit, in which a curved part of the needle has been inserted;

FIG. 10 is a partially sectional side elevation view of a sleeve made of stiff material whose body is in the form of a truncated or flared cone.

FIG. 11 is a front view of a plate constituting the gripping elements of a sleeve according to FIG. 10.

DETAILED DESCRIPTION

Figure 1:
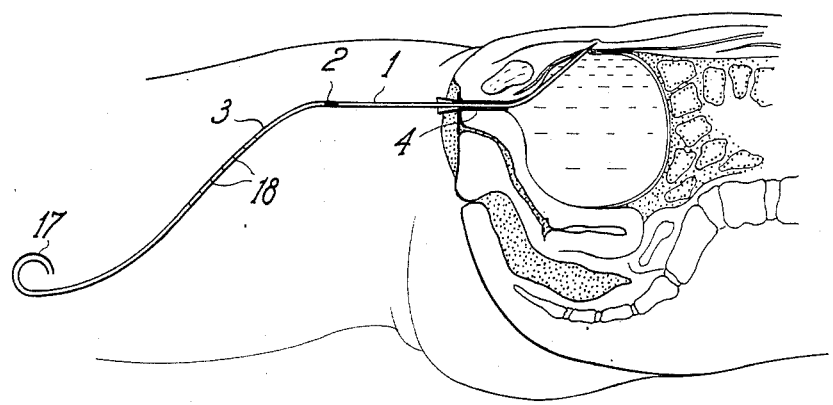
FIG. 1 shows an instrument according to the invention being introduced through the urethra.

To provide a better understanding of how to manipulate the instrument according to the invention, FIG. 1 shows such an instrument as it is being introduced through the urethra. This instrument essentially consists of: a needle 1, connected by an interlocking device 2 to a catheter 3 which constitutes the drain per se, and sleeve or sound 4. The curved needle 1 is designed to lead the catheter 3 through the urethra, pierce the wall of the bladder and the abdominal wall, and draw the end of the catheter 3, to which it is joined by the interlocking device 2, through the opening made in the wall of the bladder and abdominal wall until the posterior end of the catheter 3 is properly inserted in the bladder so that drainage will occur.

The purpose of the sleeve 4 is to make it possible for the curved needle to pass through the urethra. To correctly position the drain, however, the bladder is first filled with a physiological salt solution, and for this purpose the sleeve 4 is best provided with means for connecting it to a syringe.

The characteristics of each of the elements used will become more evident in the detailed description given below, with reference to FIGS. 2 to 12.

FIGS. 2 to 4 and 12 show various modes of realization of a needle 1 according to the invention.

In each of these embodiments, the needle, which is between 17 and 23 cm long, can be divided into a front portion, constituting the active part 5 of the needle and comprising about 2/3 of the needle, and a back portion, constituting the needle and comprising about ⅔ of the needle, and a back portion, constituting the gripping and manipulating element 6 of the needle.

In this description, the active part 5 of the needle is understood to mean that part of the needle which, in the position shown in FIG. 1, extends from the abdominal wall through the bladder and the urethra to the point of exit from the sleeve 4.

The front portion of active part 5 of the needle terminates in a sharp tip 7; the active part is also curved so that the tip 7 forms an angle a between 115 and 145° with the rear of the active part.

Figure 2:
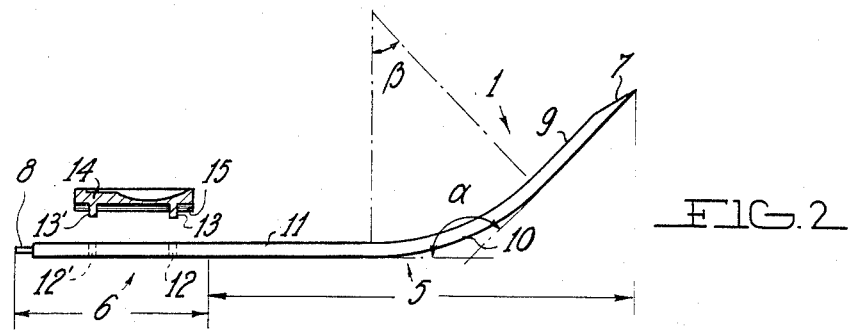
FIG. 2 is a side elevation view of a needle according to the invention.
Figure 3:
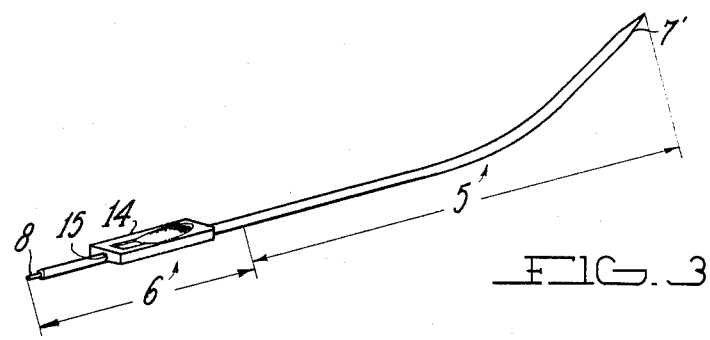
FIG. 3 is a view in perspective of another embodiment of a needle according to the invention, connected to a thumb piece.
Figure 4:
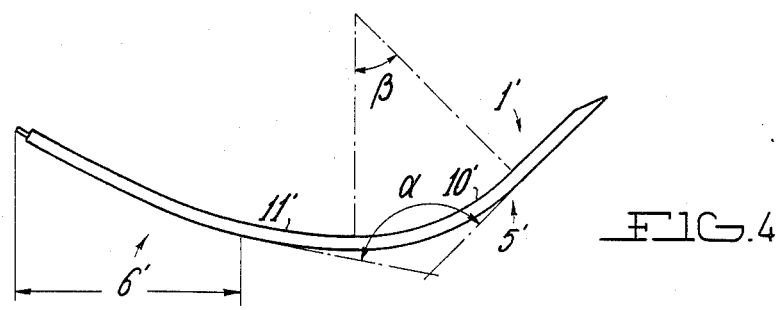
FIG. 4 is a side elevation view of still another embodiment of a needle according to the invention.

In the embodiments shown in FIGS. 2 to 4, the back portion 6 terminates in an interlocking device 8.

With reference, more specifically, to the embodiments of FIGS. 2 and 3, the front portion 5 consists of a straight head portion 9 from which the tip is formed, extended by a part in the form of an arc 10 of a circle with an angle at the center $\beta$ of 35° to 65° and a radius of curvature of 6 to 10 cm. The part in the form of an arc of a circle is connected to a straight part 11 constituting the rear of the active part 5. This straight part 11 extends to form the gripping and manipulating element 6 of the needle.

In a preferred embodiment of the invention, in the back portion of the needle making up the gripping and manipulating element 6 there is at least one seat 12 designed to accommodate a pin 13 formed on the bottom surface of a thumb piece 14, to furnish a temporary connection between said thumb piece 14 and the needle 1.

As a result, a sufficient grip on the needle 1 is provided so that it can be forced through the sleeve 4 and so that it is held securely during the piercing of the bladder and the abdominal wall.

According to the embodiment of FIG. 2, punched into the rear area of the needle there are two seats 12, 12' in the form of diametrically aligned holes designed to accommodate respective pins 13, 13' provided on the bottom surface of the thumb piece 14. The pins 13, 13' are located in a median part of a semicylindrical groove 15 in the thumb piece 14 conforming to the shape of the needle.

The embodiment of FIG. 3 is roughly the same as that of FIG. 2, except that the thumb piece 14 is shown connected to the needle and the tip 7' of the needle is a conical tip, while the tip 7 shown in FIG. 2 is a beveled tip.

In the embodiment of FIG. 4, parts 10' and 11' of the front portion 5' and the back portion 6' of the needle 1' are curved. Part 11' of the front portion and the back portion 6', however, have a greater radius of curvature than part 10'. Part 10', in the form of an arc of a circle 10', defines an angle $\beta$ of 35° to 65°.

FIG. 5 shows a larger-scale representation of the interlocking device 2 between the needle 1 and the catheter 3, consisting of a screw 8 provided at the rear extremity of the needle 1 and a threaded recess 8' located on the front of the catheter 3.

FIG. 6 shows, again on a larger scale, an interlocking device 2' between a needle 1 and a catheter 3, consisting of a pin 8", coaxial to the needle and whose diameter matches the internal diameter of tube 16 in the catheter 3, pin 8" is shown inserted into the tube 16. The needle and the catheter are joined by an adhesive holding the pin 8" in the tube 16, for example.

In any circumstances care must be taken to see that the outer dimensions in cross-section of the catheter 3, up to and including the location of the interlocking device 2 for connection to the needle, do not exceed the outer dimensions in crosssection of the needle 1.

The catheter 3 will preferably be one with a preformed loop-shaped end 17, as shown in FIG. 1, which resumes its shape after passing through the urethra. The drainage opening of such catheters are located on the inner surface of the loop.

In a preferred embodiment of the invention, reference marks 18, preferably annular, are provided on the outer wall of the catheter to indicate the distance between that point and the drainage end of the loop of the catheter.

FIGS. 7 to 10 show various embodiments of a sleeve or sound 4 according to the invention, designed to make it possible for the needle 1 and the catheter 3 to pass through the urethra.

In the enbodiment of FIG. 7, the sleeve essentially consists of a body 19, normally straight, but flexible enough to deform elastically in the manner shown in FIG. 7 when the curved part 10 of the needle passes through it. The inner diameter of the body of the sleeve 19 is slightly greater than the outer diameter of the needle.

With reference to the embodiment in FIG. 8, the sleeve 4 consists of a curved flexible body 19' which connects to a flared opening 20 at the rear. In this embodiment, the curvature of the body 19' roughly matches the curvature of the curved part 10 of the needle. In this case, also, the sleeve is so constructed that it is flexible enough to deform in an elastic manner when the needle passes through it, with the deformation occurring, however, when the straight part of the needle passes through.

In the embodiment of FIG. 9, the sleeve 19" is formed as a straight, slitted tube the flexibility of which is created, or at least enhanced, by the presence of a lengthwise slit 21 extending from the front end of the body over a distance which is between half and all of the length of the body. The slit 21 opens upon passage of the curved part 10 of the needle to give the body 19" the requisite flexibility.

In the embodiment of FIG. 10, a sleeve 4' is made of a stiff material and has a truncated-cone-shaped body 19''' whose diameter increases from its anterior part 22 to its posterior part 23. The inner dimensions of the body are adequate to allow the curved part 10 of the needle to pass through. The body 19''' is connected at its posterior end to a flared opening 20' by which it can be connected to a syringe. The body 19''' is also joined at its posterior end to a gripping element 24 which is in the form of a plate. In a preferred embodiment of the invention, the plate 24 is detachable and is in the form shown in FIG. 11, for example. This has a generally elongated shaped and is provided with a hole 25 through which the body of the sleeve 19''' passes; the plate is prevented from slipping off the sleeve 19''' by the flared opening 20' when it is installed onto the body 19'''.

The plate 24 serves as a retaining device for the sleeve 4 when the latter is subjected to deformation or stress during the passage of the needle, and as a gripping device when the drainage end has been positioned, permitted withdrawal of the sleeve from the urethra.

Figure 12:
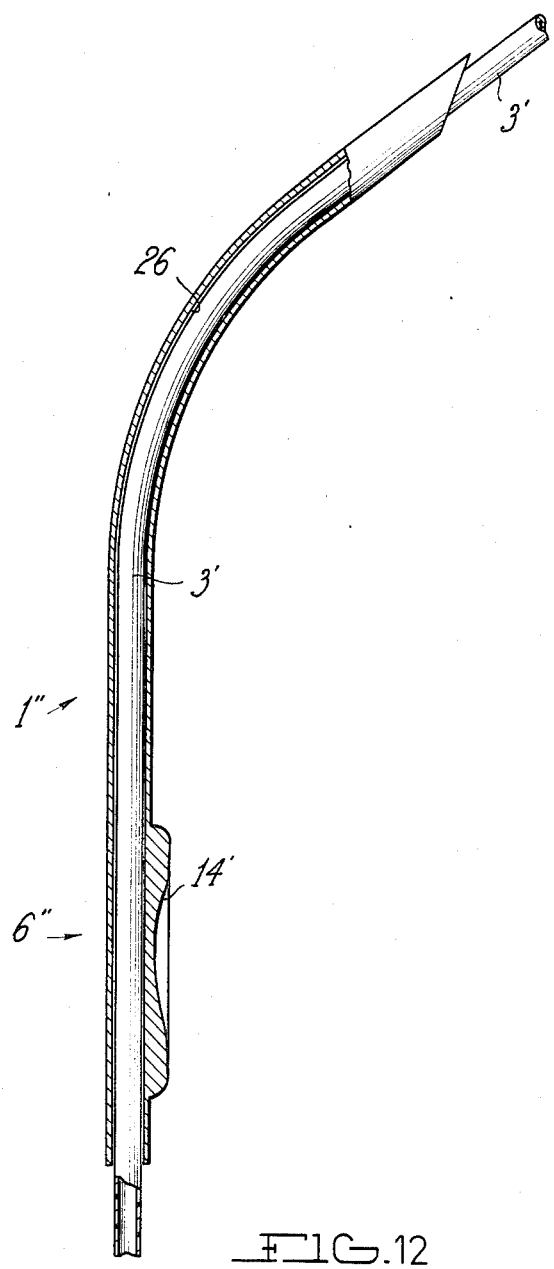
FIG. 12 is a partially sectional side elevation view of another embodiment of a needle and a catheter according to the invention.

In the embodiment of FIG. 12, the needle 1" is hollow and thus contains a lengthwise canal 26 extending over its entire length, through which a catheter 3' can be passed.

The back portion 6", constituting the gripping and manipulating element, of the needle 1 also has a thumb piece 14, which, in the example shown, is a part of the needle 1".

In practice, this arrangement permits extremely fast, easy introduction of a suprapubic bladder drainage instrument, as follows.

The sleeve 4 is first introduced into the urethra. It is then connected to a syringe in order to fill the bladder with a physiological salt solution. The syringe is then disconnected and the needle 1, joined to the catheter 3, is then introduced through the sleeve 4. The needle 1 is forced through the sleeve, while the plate 24 keeps the latter in place, even when it is subjected to stresses to bring about a given deformation so that the needle can pass through. The curved shape of the needle allows it to circumvent the symphysis and pierce the wall of the bladder to reach the abdominal wall.

When a needle such as that shown in FIGS. 2 to 4 is used, once the various tissues have been tranversed, the needle 1 is disconnected from the thumb piece 14, if such a piece has been used, and is withdrawn from the opening formed, drawing the catheter 3 after it. The reference marks 18 are used to determine the length of catheter remaining in the bladder, and the catheter is then cut to the desired length and connected to a conventional collection device, consisting of a hermetically sealed flexible container, for example, and a valve to permit or interrupt the flow of urine.

On the other hand, when a hollow needle such as that shown in FIG. 12 is used, once the various tissues have been transversed, a catheter 3' is introduced into the needle and is advanced through the needle 1" until it occupies the proper position for drainage of the bladder.

The needle is then withdrawn, taking care to see that the catheter remains in place.

With the use of a needle according to the embodiments of FIGS. 2 to 4, the needle can be withdrawn through the opening made in the tissues.

A needle of the type shown in FIG. 12 can also be withdrawn through the urethra, reversing the path taken to reach the abdominal wall. In such cases the back portion 6" remains outside the body of the patient, and the thumb piece 14' thus can be a part of the needle 1" without creating any withdrawal problems.

The instrument according to the invention can be manufactured economically as a disposable set provided in sterile packaging.

The invention has been described and illustrated merely by way of example and in no way restrictive. Numerous changes in its construction may be made without departing from the spirit of the invention.

What is claimed is:

1. A needle for introducing a suprapubic bladder drainage instrument through the urethra, said needle including:
    a rigid front portion terminating at a front end in a sharp tip and having a rear;
    a rigid back portion constituting a gripping and manipulating element of the needle and joined to the rear of said front portion;
    the rigid front portion including a curved part, the curvature being such that the tip is angled at between 115° and 145° to the rear of the front portion;
    means for connecting the needle to a catheter; and
    deformable guide means for introducing said needle as connected to said catheter into the urethra wherein,
    the needle is sufficiently rigid to maintain said curved part during insertion into the bladder and puncture of the bladder wall, and
    said deformable guide means conforms to said curved part.

2. The needle according to claim 1, characterized in that:
    the front rigid portion includes a straight head portion from which the tip is formed;
    the curved part being in the form of an arc of a circle with an angle at the center of 35° to 65° and a radius of curvature of 6 to 10 cm;
    the curved part being connected to a straight part constituting the rear of the front rigid portion and extending to form the rear rigid portion comprising the gripping and manipulating element.

3. A needle for introducing a suprapubic bladder drainage instrument through the urethra, said needle including:
    a front portion terminating at a front end in a sharp tip and having a rear;
    a back portion constituting a gripping and manipulating element of the needle and joined to the rear of said front portion;
    the front portion including a curved part, the curvature being such that the tip is angled at between 115° and 145° to the rear of the front portion;
    means for connecting the needle to a catheter; and
    a thumb piece having at least one connecting pin;
    the back portion of the needle making up the gripping and manipulating element has at least one seat to accommodate the pin of said thumb piece, to furnish a temporary connection between said thumb piece and the needle.

4. The needle according to claim 3, characterized in that said at least one seat includes at least two diametrically aligned holes in the back portion of the needle;
    two pins are formed on the bottom surface of the thumb piece, adapted for temporary locking with said holes and located in a median part of a semicylindrical groove of said thumb piece which groove conforms to the shape of the needle.

5. The needle according to claim 1, characterized in that the front rigid portion and the back rigid portion of the needle are curved.

6. The needle according to claim 1, characterized in that the means for connection with a catheter includes an interlocking device provided at the end of the back rigid portion of the needle.

7. The needle according to claim 6, characterized in that:
    the interlocking device at the end of the back rigid portion of the needle is one of the elements of a screw-threaded interlocking device; and
    the outer dimensions of the interlocking device in cross-section do not exceed the outer dimensions of the needle in cross-section.

8. The needle according to claim 6, characterized in that:
    the interlocking device at the end of the back rigid portion of the needle is a stud coaxial with the needle whose diameter is adapted to match the inner diameter of a catheter; and
    said stud is adapted to be inserted into the front end of said catheter and to be adhesively secured there.

9. The needle according to claim 1, characterized in that the means for connection to a catheter includes a lengthwise canal inside the needle through which the catheter can pass.

10. The needle according to claim 6, wherein said catheter includes:
    at its front end an interlocking device which mates with the interlocking device provided at the end of the back portion of the needle;
    the dimensions of the catheter in cross-section being no greater than the outer dimensions of the needle in cross-section.

11. A needle for introducing a suprapubic bladder drainage instrument through the urethra, said needle including:
    a front portion terminating at a front end in a sharp tip and having a rear;
    a back portion constituting a gripping and manipulating element of the needle and joined to the rear of said front portion;
    the front portion including a curved part, the curvature being such that the tip is angled at between 115° and 145° to the rear of the front portion;
    means for connecting the needle to a catheter;
    means for introducing said needle as connected to said catheter into the urethra;
    an interlocking device provided at the end of the back portion of the needle; and
    an interlocking device which mates with the catheter front end and with the interlocking device provided at the end of the back portion of the needle;

said catheter includes a drainage end, wherein reference marks are provided on the outer surface of said catheter which indicate the distance between the mark and the drainage end of the catheter, and the dimensions of the catheter in cross-section being no greater that the outer dimensions of the needle in cross-section.

12. An instrument for suprapubic drainage of the bladder adapted for insertion through the urethra including:

a catheter;

a rigid curved needle having a cutting point;

means for attaching said catheter to said rigid curved needle; and a deformable sleeve adapted to permit the passage of said rigid curved needle and said cutting point and catheter into the bladder through the urethra;

wherein said cutting point is the anterior part of said rigid curved needle and said rigid curved needle being at least the length of said sleeve, said rigid curved needle is sufficiently rigid to maintain the needle curvature during insertion into the bladder and puncture of the bladder wall, and said deformable sleeve conforms to said rigid curved needle.

* * * * *

UNITED STATES PATENT AND TRADEMARK OFFICE
CERTIFICATE OF CORRECTION

PATENT NO.  : 4,684,369
DATED       : August 4, 1987
INVENTOR(S) : Dirk A.A. Wildemeersch It is certified that error appears in the above-identified patent and that said Letters Patent is hereby corrected as shown below:

| | | |
|---|---|---|
| Column 1, | line 20, | "used on" should read --used in-- |
| Column 2, | line 7, | "stright" should read --straight-- |
| | line 39, | "crosssection" should read --cross-section-- |
| Column 3, | line 63, | "passing" should read --passage-- |
| Column 4, | line 5, | "elements" should read --element-- |
| | line 22, | "and abdominal" should read --and the abdominal-- |
| Column 4, | lines 40-41 | "constituting the needle and comprising about $\frac{2}{3}$ of the needle, and a back portion, constituting the gripping" should read --constituting the gripping-- |
| | line 48, | "portion of" should read --portion or-- |
| | line 50, | "angle a between" should read --angle $\alpha$ of between-- |
| Column 5, | line 42, | "crosssection" should read --cross-section-- |
| | line 46, | "opening" should read --openings-- |
| | line 57, | "enbodiment" should read --embodiment-- |

UNITED STATES PATENT AND TRADEMARK OFFICE
CERTIFICATE OF CORRECTION

PATENT NO. : 4,684,369

DATED : August 4, 1987

INVENTOR(S) : Dirk A.A. Wildemeersch

It is certified that error appears in the above-identified patent and that said Letters Patent is hereby corrected as shown below:

Column 6, line 59, "tranversed," should read --traversed,--

Column 7, line 3, "transversed," should read --traversed,--

Signed and Sealed this

Sixth Day of December, 1988

Attest:

DONALD J. QUIGG

Attesting Officer

Commissioner of Patents and Trademarks